(12) United States Patent
Ikeda et al.

(10) Patent No.: US 8,460,179 B2
(45) Date of Patent: Jun. 11, 2013

(54) BALLOON UNIT FOR ENDOSCOPE APPARATUS

(75) Inventors: Toshiyuki Ikeda, Saitama (JP); Syuuji Komi, Saitama (JP); Isao Watanabe, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 447 days.

(21) Appl. No.: 11/783,845

(22) Filed: Apr. 12, 2007

(65) Prior Publication Data

US 2007/0244361 A1    Oct. 18, 2007

(30) Foreign Application Priority Data

Apr. 13, 2006   (JP) .................................. 2006-110955

(51) Int. Cl.
*A61B 1/00*   (2006.01)

(52) U.S. Cl.
USPC ........................................................ 600/115

(58) Field of Classification Search
USPC .............. 606/195; 604/103.01; 600/116, 115, 600/101, 104, 114
See application file for complete search history.

(56) References Cited

U.S. PATENT DOCUMENTS

| | | | | |
|---|---|---|---|---|
| 4,441,495 A | * | 4/1984 | Hicswa | 606/195 |
| 4,517,979 A | * | 5/1985 | Pecenka | 606/195 |
| 4,779,624 A | * | 10/1988 | Yokoi | 600/439 |
| 4,957,486 A | * | 9/1990 | Davis | 604/102.02 |
| 4,961,738 A | * | 10/1990 | Mackin | 606/15 |
| 5,163,950 A | * | 11/1992 | Pinchuk et al. | 606/192 |
| 5,569,215 A | * | 10/1996 | Crocker | 604/264 |
| 5,707,382 A | * | 1/1998 | Sierocuk et al. | 606/190 |
| 6,629,924 B2 | * | 10/2003 | Aydelotte | 600/120 |
| 6,743,208 B1 | * | 6/2004 | Coyle | 604/164.13 |
| 6,960,163 B2 | * | 11/2005 | Ewers et al. | 600/114 |
| 6,972,040 B2 | * | 12/2005 | Rioux et al. | 623/23.66 |
| 2005/0215855 A1 | * | 9/2005 | Machida | 600/114 |
| 2006/0241345 A1 | | 10/2006 | Oishi et al. | |

FOREIGN PATENT DOCUMENTS

| | | |
|---|---|---|
| CA | 1322967 | 10/1993 |
| EP | 0 362 436 B1 | 4/1990 |
| JP | 2-023987 A | 9/1990 |
| JP | 2-239874 A | 9/1990 |
| JP | 5-15487 A | 1/1993 |
| JP | 5-285090 A | 11/1993 |
| JP | 7-313433 A | 12/1995 |
| JP | 7-313443 A | 12/1995 |
| WO | WO 2004/012628 * | 2/2004 |
| WO | WO 2004-067080 A1 | 8/2004 |

* cited by examiner

*Primary Examiner* — Gary Jackson
*Assistant Examiner* — Lindsey Bachman
(74) *Attorney, Agent, or Firm* — Birch, Stewart, Kolasch & Birch, LLP

(57) ABSTRACT

The present invention provides a balloon unit for an endoscope apparatus comprising: a balloon for an endoscope apparatus having an opening formed in a cylindrical shape in which an insert part of an endoscope or an insert supporter having the insert part inserted therein is inserted and fixed; and a cylinder body having an inner diameter larger than an outer diameter of the insert part or the insert supporter; wherein the opening of the balloon is fitted over and fixed to the cylinder body to form a unit and the unit is attached to the insert part or the insert supporter or detached from the insert part or the insert supporter.

4 Claims, 10 Drawing Sheets

BALLOON UNIT FOR ENDOSCOPE APPARATUS

BACKGROUND OF THE INVENTION

1. Field of the Invention

The present invention relates to a balloon unit for an endoscope apparatus, and particularly relates to a balloon unit for an endoscope apparatus which is attached to an endoscope for observing small bowel and large bowel.

2. Description of the Related Art

In endoscope apparatuses, balloons which can expand and contract are used for various purposes. For example, in an endoscope apparatus for observing deep alimentary canals such as small bowel and large bowel, an expandable balloon is attached to an endoscope insert part or an endoscope insert supporter (such as a sliding tube or an over tube), so that the endoscope insert part or the insert supporter can be fixed to a viscera by expanding the balloon. In an ultrasonic diagnosis apparatus, an expandable balloon is used to surround an ultrasonic scan part at a tip of an ultrasonic probe and fill an ultrasonic transmitting medium. In an ultrasonic endoscope, an expandable balloon is used to surround an ultrasonic transducer at a tip of an insert part and fill an ultrasonic transmitting medium.

Such a balloon for endoscope is made of an elastic body such as rubber and an end of the balloon is formed in a cylindrical shape having a diameter smaller than an outer diameter of an object to be attached (the endoscope insert part or the insert supporter, for example). When the balloon is attached, the object to be attached is covered with the end of the balloon while enlarging the diameter of the end. Thereafter, thread is wound or a rubber band is fitted over the end of the balloon so as to fix the end of the balloon to the object to be attached.

However, there is a problem that the task of covering the object to be attached with the end of the balloon while enlarging the diameter of the end of the balloon is very onerous and the attachment task is troublesome.

Thus, in Japanese Patent Application Laid-Open No. 5-15487, a method is described in which a balloon is adsorbed and attached on an inner circumferential surface of a cylinder body. According to this method, an inner diameter of the balloon can be enlarged by adsorbing the balloon on the inner circumferential surface of the cylinder body, so that the insert part or the insert supporter can be easily inserted therethrough.

However, the attachment method in Japanese Patent Application Laid-Open No. 5-15487 has problems that a special attachment jig is required and a task of attaching the special attachment jig to the balloon is troublesome and thus the balloon can not be quickly attached.

In addition, the method in Japanese Patent Application Laid-Open No. 5-15487 is adapted to attach a balloon to an endoscope having a fluid supplying and sucking port in an outer circumferential surface of an insert part. If there is no fluid supplying and sucking port in the insert part, it is necessary to insert a tip of a tube deeply into the balloon. Therefore, there are problems that the task of attaching the balloon is troublesome and air-tightness between the balloon and the insert part after attachment is low.

The present invention is provided in view of the above problems and it is an object of the present invention to provide a balloon unit for an endoscope apparatus which can be quickly and easily attached to an object to be attached such as an endoscope insert part or an insert supporter.

SUMMARY OF THE INVENTION

To accomplish the above object, a first aspect of the present invention provides a balloon unit for an endoscope apparatus comprising: a balloon for an endoscope apparatus having an opening formed in a cylindrical shape in which an insert part of an endoscope or an insert supporter having the insert part inserted therein is inserted and fixed, and a cylinder body having an inner diameter larger than an outer diameter of the insert part or the insert supporter, wherein the opening of the balloon is fitted over and fixed to the cylinder body to form a unit and the unit is attached to the insert part or the insert supporter or detached from the insert part or the insert supporter.

According to the first aspect, because the opening (the end) of the balloon is fitted over the cylinder body to form a unit, the insert part or the insert supporter can be easily covered with the end of the balloon by inserting the insert part or the insert supporter through the cylinder body.

A second aspect of the present invention is that, in the first aspect, a tube for supplying and sucking fluid into/from the balloon for an endoscope apparatus is connected to the cylinder body.

According to the second aspect of the invention, because the tube for supplying and sucking fluid is connected to the cylinder body, the balloon can be also attached to an endoscope even having no duct for supplying and sucking fluid in its insert part, so as to provide a balloon(-equipped) endoscope. That is, according to the second aspect, even if an endoscope is not a special endoscope having a duct for supplying and sucking fluid in its insert part, the balloon unit can be afterwards attached to the endoscope to provide a balloon endoscope.

A third aspect of the present invention is that, in the second aspect, a flow passage for supplying and sucking fluid into/from the balloon for an endoscope apparatus is formed in the cylinder body and the tube is connected to an end of the flow passage.

According to the third aspect of the invention, because the flow passage is formed in the cylinder body and the tube is connected to the flow passage, it is not necessary to insert the tube deeply into the balloon. Therefore, the task of attaching the balloon can be easily performed and air-tightness in the fixing part (the opening) of the balloon can be sufficiently ensured.

A fourth aspect of the present invention is that, in the third aspect, in the end of the flow passage of the cylinder body, a connector is provided to which the tube is detachably connected.

According to the fourth aspect of the invention, because the connector is provided in the end of the flow passage of the cylinder body, the tube can be detachably connected. Therefore, the tube can be connected to the connector after inserting the insert part or the insert supporter through the cylinder body and thus the task of inserting the insert part or the insert supporter through the cylinder body can be easily performed.

A fifth aspect of the present invention is that, in any one of the first to fourth aspects, a doughnut-shaped balloon for attachment, through which the insert part or the insert supporter is inserted, is provided on an inner side of the cylinder body, and the cylinder body is fixed to the insert part or the insert supporter by expanding the balloon for attachment so that the balloon for attachment presses an outer circumferential surface of the insert part or the insert supporter.

According to the fifth aspect of the invention, because the cylinder body is fixed to the insert part or the insert supporter by expanding the balloon for attachment, the cylinder body can be reliably fixed regardless of diameter of the insert part or the insert supporter.

In addition, in the fifth aspect of the invention, the feature of expanding and fixing the balloon for attachment allows large clearance between the inner circumferential surface of the cylinder body and the outer circumferential surface of the insert part or the insert supporter, so that the insert part or the insert supporter can be easily inserted through the cylinder body.

Further, according to the fifth aspect of the invention, a gap between the outer circumferential surface of the insert part or the insert supporter and the inner circumferential surface of the cylinder body can be reliably sealed by the balloon for attachment.

In the fifth aspect, it is preferable to provide a device which controls supply pressure of fluid supplied to the balloon for attachment, depending on the outer diameter dimension of the insert part or the insert supporter.

A sixth aspect of the present invention is, in the first aspect, a flow passage for supplying and sucking fluid into/from the balloon for an endoscope apparatus is formed in the cylinder body; a doughnut-shaped balloon for attachment, through which the insert part or the insert supporter is inserted, is provided on an inner side of the cylinder body, and the cylinder body is fixed to the insert part or the insert supporter by expanding the balloon for attachment so that the balloon for attachment presses an outer circumferential surface of the insert part or the insert supporter; and further the flow passage of the cylinder body is branched to communicate with the balloon for attachment; and a branch passage of the flow passage is provided with a check valve.

According to the sixth aspect of the invention, because the flow passage of the cylinder body is branched to communicate with the balloon for attachment, the balloon for attachment can be expanded by the fluid which is used to expand the balloon. In addition, according to the sixth aspect of the invention, because the branch part of the flow passage is provided with a check valve, fluid does not flow out from the balloon for attachment when air is sucked from the balloon to contract the balloon. Thus, contraction of the balloon for attachment can be prevented.

According to the present invention, because the opening (the end) of the balloon is fitted over the cylinder body to form a unit, the insert part or the insert supporter can be easily covered with the end of the balloon by inserting the insert part or the insert supporter through the cylinder body. Therefore, the task of attaching the balloon can be easily performed.

DETAILED DESCRIPTION OF THE PREFERRED EMBODIMENTS

Now, preferred embodiments of a balloon unit for an endoscope apparatus according to the present invention will be described in detail with reference to the accompanied drawings.

Figure 1:
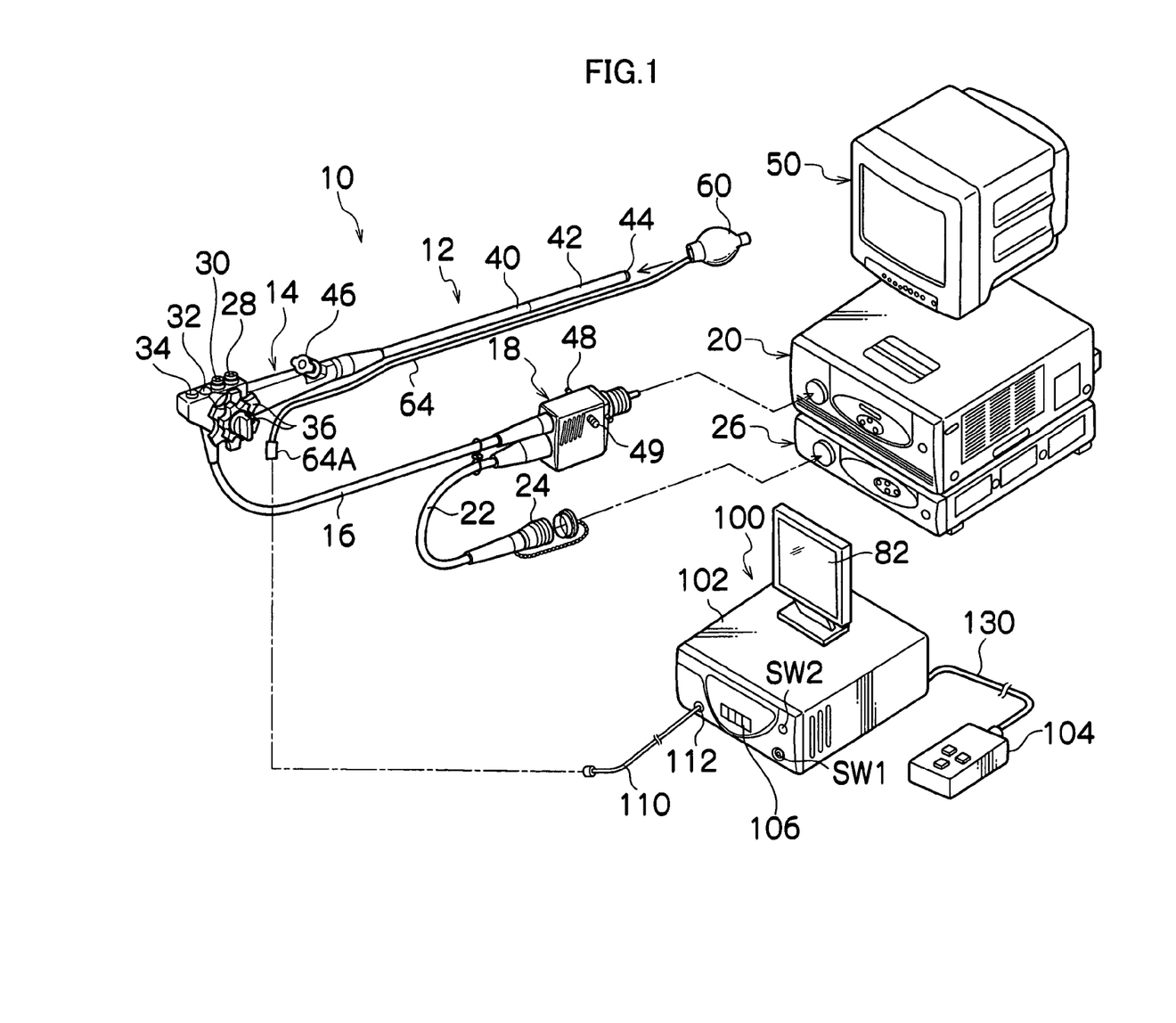
FIG. 1 is a system configuration view of an endoscope apparatus to which a balloon unit for an endoscope apparatus according to the present invention is applied.

FIG. 1 is a system configuration view showing an example of an endoscope apparatus to which the balloon unit for an endoscope apparatus according to the present invention is applied. As shown in FIG. 1, the endoscope apparatus mainly includes an endoscope 10, a balloon for an endoscope apparatus (referred to as a balloon, hereinafter) 60, and a balloon controlling apparatus 100.

The endoscope 10 includes a hand operating part 14 and an insert part 12 which is connected to the hand operating part 14 and is to be inserted into a body cavity. A universal cable 16 is connected to the hand operating part 14 and a LG connector 18 is provided at a tip of the universal cable 16. The LG connector 18 is detachably coupled to a light source apparatus 20 so that illumination light is transmitted to an illumination optics (not shown) provided at a tip of the insert part 12. In addition, an electrical connector 24 is connected to the LG connector 18 via a cable 22 and the electrical connector 24 is detachably coupled to a processor 26.

In the hand operating part 14, an air/water supply button 28, a suck button 30, a shutter button 32, and a function switch button 34 are provided side by side and a pair of angle knobs 36, 36 is provided.

The insert part 12 is composed of a soft part 40, a bend part 42, and a tip part 44 in this order from the side of the hand operating part 14. The soft part 40 is made by covering an outer circumference of a metal plate, which is wound in a spiral shape, with a net and further covering the outer circumference with a coating, so that the soft part 40 has sufficient flexibility. The soft part 40 is connected to a base end of the bend part 42.

The bend part 42 is configured to be remotely bent by turning the angle knobs 36, 36 of the hand operating part 14. For example, in the bend part 42, a plurality of cylindrical sections are rotatably coupled by pins and a plurality of operating wires are inserted into the sections through and guided by the pins so that the operating wires are moved forward and backward. Thereby, the sections rotate with respect to each other to bend the bend part 42. By bending the bend part 42, the tip part 44 can be oriented in a desired direction.

Although not shown, the tip part 44 is provided with an observation optics, an illumination optics, an air/water supply nozzle, and a forceps port on its tip surface, for example. A CCD is disposed behind the observation optics and a signal cable is connected to a substrate which supports the CCD. The signal cable is inserted through the insert part 12, the hand operating part 14, the universal cable 16 and the like and extended to the electrical connector 24 so that the cable is connected to the processor 26. Therefore, an observed image captured by the observation optics is focused on a light receiving surface of the CCD and converted into an electrical signal. Then, the electrical signal is output to the processor 26 through the signal cable and converted into an image signal.

As a result, the observed image is displayed on a monitor 50 which is connected to the processor 26.

An output end of a light guide is positioned behind the illumination optics, and the light guide is inserted through the insert part 12, the hand operating part 14, and the universal cable 16 so that an input end of the light guide is positioned in the LG connector 18. Therefore, by coupling the LG connector 18 to the light source apparatus 20, illumination light radiated from the light source apparatus 20 is transmitted through the light guide to the illumination optics and radiated forward from the illumination optics.

The air/water supply nozzle is linked to a valve which is operated with the air/water supply button 28 and the valve is linked to an air/water supply connector 48 which is provided in the LG connector 18. An air/water supplying device (not shown) is connected to the air/water supply connector 48 to supply air and water. Therefore, by operating the air/water supply button 28, air or water can be sprayed from the air/water supply nozzle toward the observation optics.

The forceps port is communicated with a forceps insert part 46. Therefore, by inserting an operative instrument such as a forceps from the forceps insert part 46, the operative instrument can be guided out through the forceps port. In addition, the forceps port is linked to a valve which is operated with the suck button 30 and the valve is connected to a suck connector 49 of the LG connector 18. Therefore, by connecting a sucking device (not shown) to the suck connector 49 and actuating the valve with the suck button 30, lesions and the like can be sucked from the forceps port.

Figure 2:
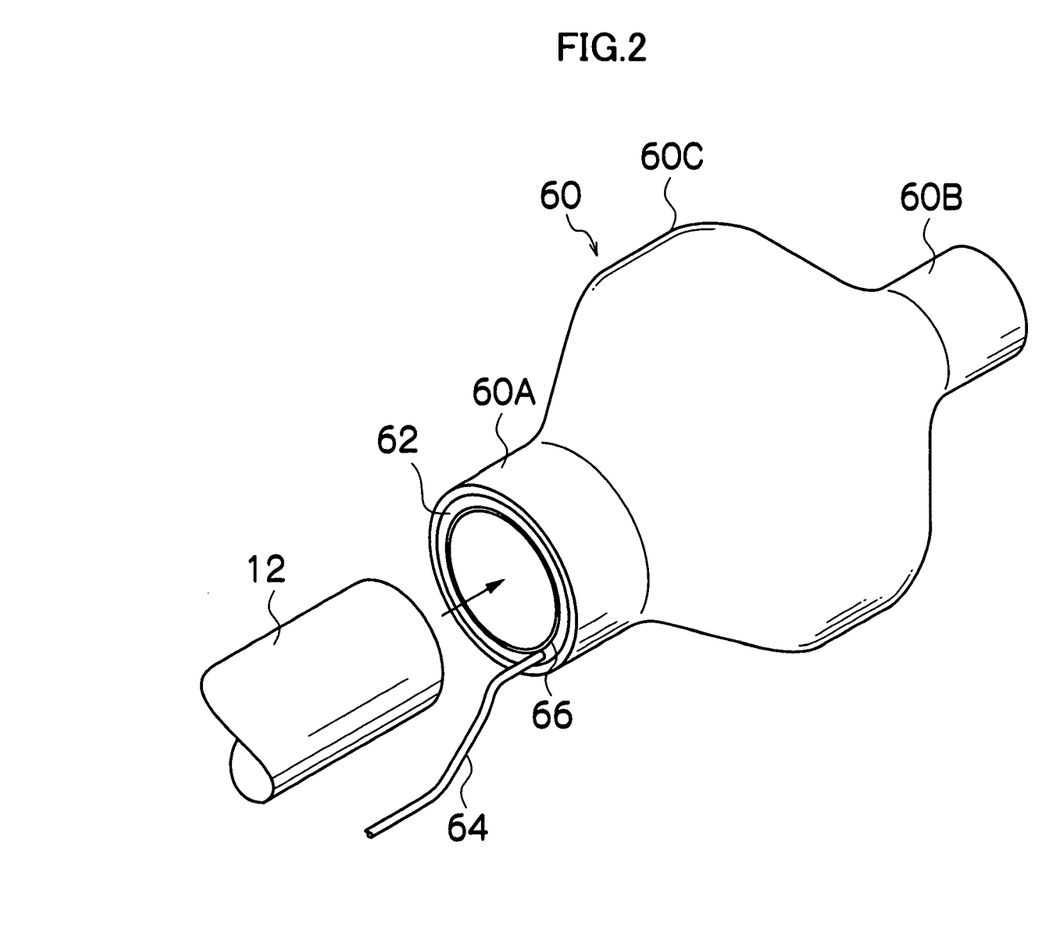
FIG. 2 is a perspective view showing the balloon unit.
Figure 3:
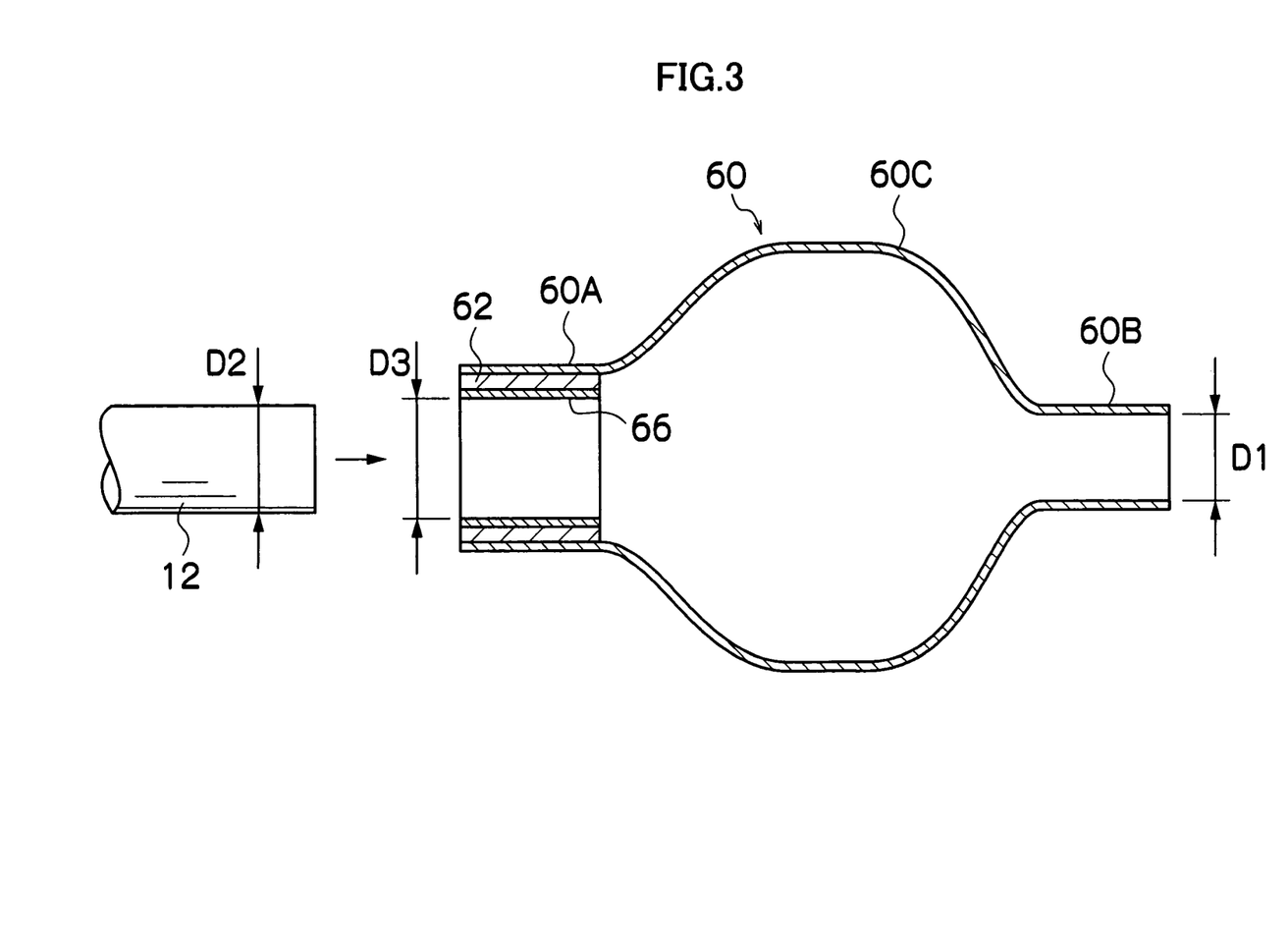
FIG. 3 is a cross sectional view of the balloon unit in FIG. 2.

As shown in FIGS. 2 and 3, the balloon 60 is formed in a generally cylindrical shape with narrow both ends and the balloon 60 is composed of ends 60A, 60B having a small diameter and a center swelled part 60C. The balloon 60 is made of an elastic material such as natural rubber, silicone rubber or the like and is positioned and fixed in a predetermined position (the soft part 40, for example) of the insert part 12, by inserting the insert part 12 through the balloon 60.

The end 60B of the balloon 60 has an inner diameter D1 (see FIG. 3) formed somewhat smaller than an outer diameter D2 of the insert part 12. By inserting the insert part 12 through while elastically deforming the end 60B to enlarge its diameter, the end 60B tightly contacts the whole outer circumferential surface of the insert part 12 after attachment. Thus, there is no gap between the end 60B and the insert part 12 so that high air-tightness can be obtained.

The end 60A of the balloon 60 is fitted over and fixed to a hard cylinder body 62 so that a balloon unit is configured by the cylinder body 62 and the balloon 60. The end 60A of the balloon 60 has an inner diameter formed somewhat smaller than the outer diameter of the cylinder body 62 and is fitted over the cylinder body 62 while elastically deforming the end 60A to enlarge its diameter. As a result, the end 60A is fixed in such a manner that it tightly contacts the whole outer circumferential surface of the cylinder body 62. The end 60A of the balloon 60 and the cylinder body 62 are fixed, for example, by winding thread on the outer side of the end 60A or by applying and solidifying adhesive, although not particularly limited to these.

The cylinder body 62 is formed in a cylindrical shape with a material which can keep its shape such as metal or resin. The cylinder body 62 may be made of one material or may be made of two or more materials by applying and solidifying melt resin on the outer circumference of a metal ring, for example.

Figure 4:
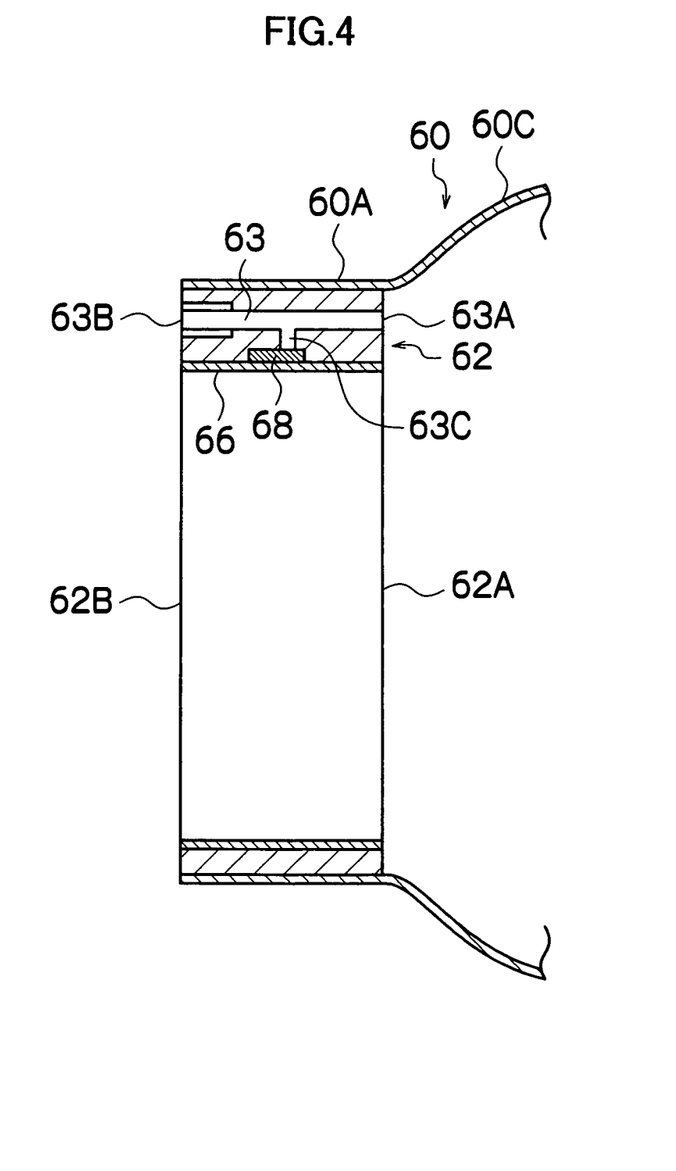
FIG. 4 is a cross sectional view showing a cylinder body.

As shown in FIG. 4, the flow passage (hole) 63 is provided in the cylinder body 62. The flow passage 63 is formed in an axial direction of the cylinder body 62 and opened in both end surfaces. In other words, the flow passage 63 has an opening 63A in an inner end surface (the right end surface in FIG. 4) 62A of the balloon 60 and an opening 63B in an outer end surface (the left end surface in FIG. 4) of the balloon 62B. In addition, the flow passage 63 is branched halfway and a tip of a branch passage 63C is opened in the inner circumferential surface of the cylinder body 62 and an inner side of the balloon for attachment 66.

Figure 6:
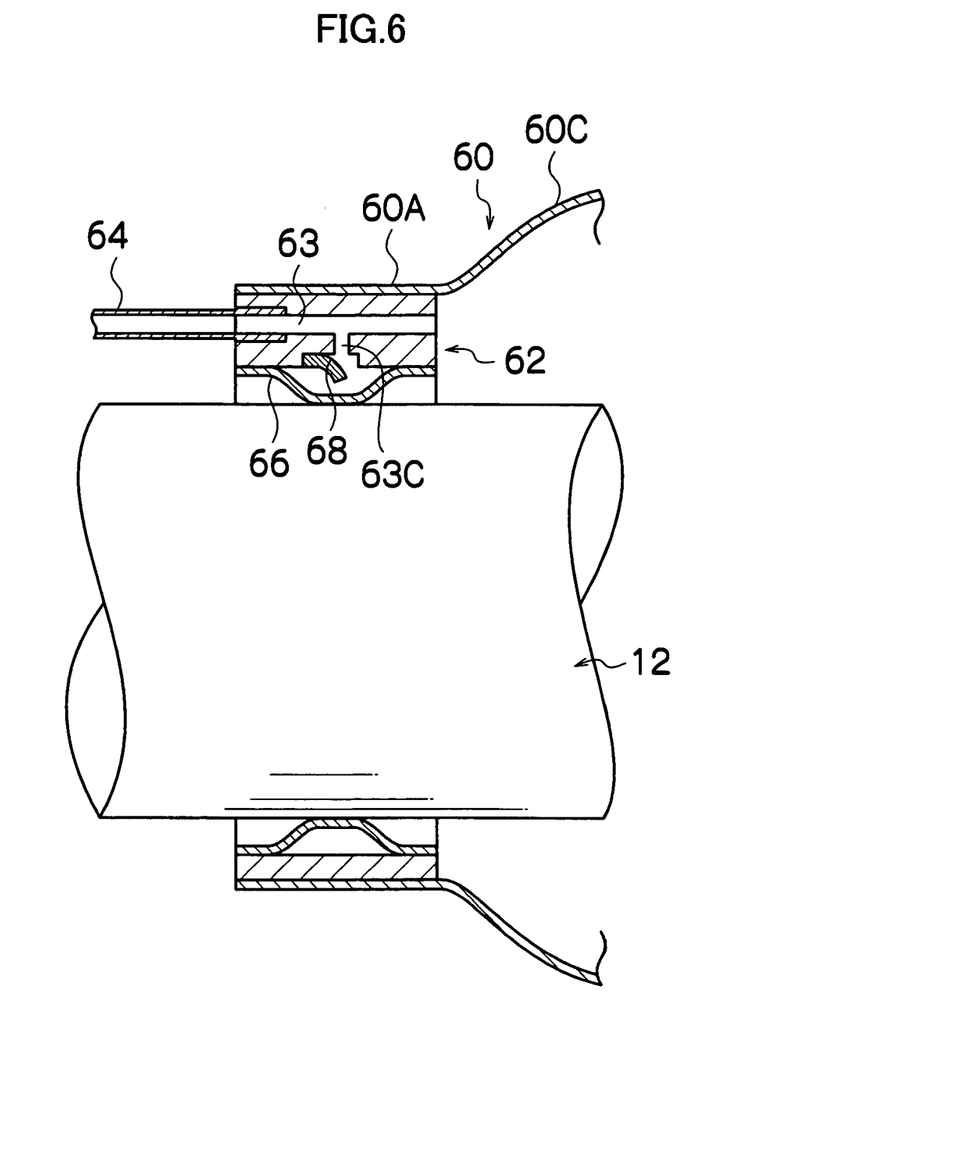
FIG. 6 is a cross sectional view showing the cylinder body fixed to the insert part.

The balloon for attachment 66 is formed in a cylindrical shape with an elastic body such as rubber and fixed on the inner circumferential surface of the cylinder body 62. In both ends of the balloon for attachment 66, its whole outer circumferential surface is stuck on the inner circumferential surface of the cylinder body 62, so that the balloon for attachment 66 is expanded in a doughnut shape as shown in FIG. 6 by supplying fluid from the branch passage 63C to the balloon for attachment 66.

Figure 5:
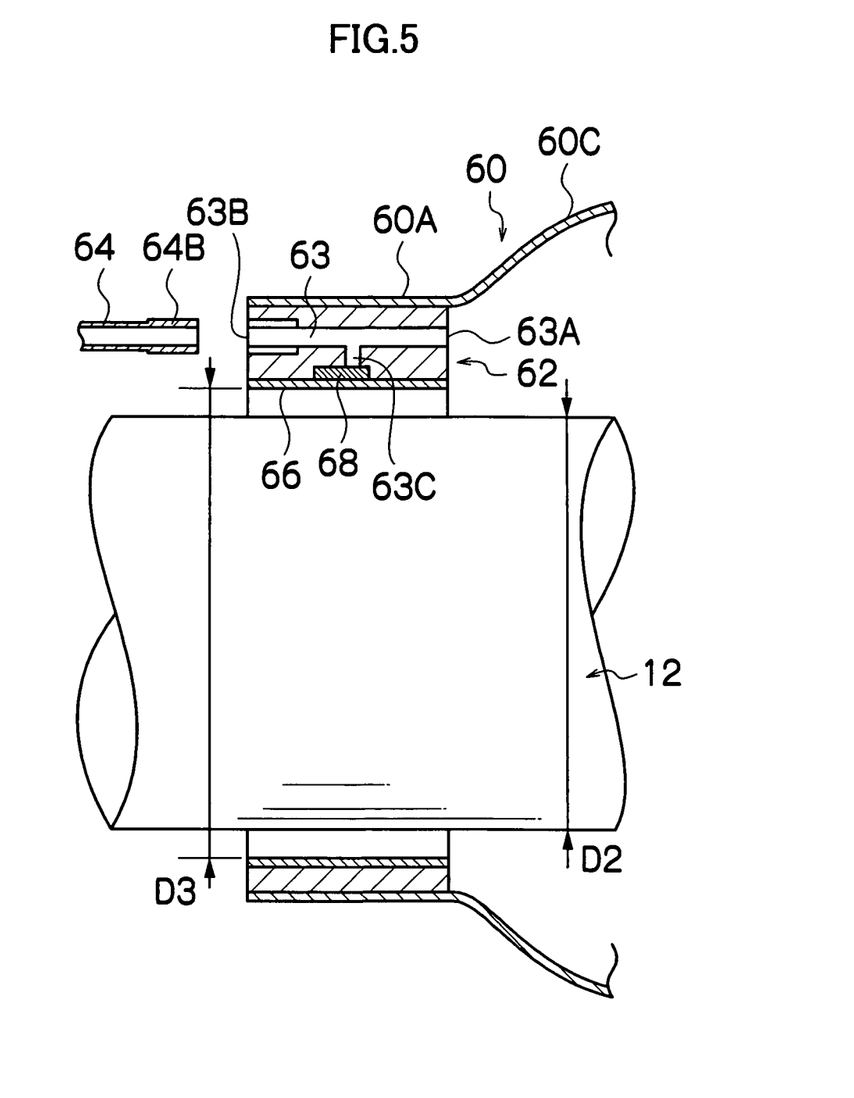
FIG. 5 is a cross sectional view showing the cylinder body through which an insert part is inserted.

The balloon for attachment 66 has an inner diameter D3 (see FIG. 3) formed somewhat larger than the outer diameter D2 of the insert part 12 when it is contracted as shown in FIG. 5, so that the insert part 12 can be inserted through the inner cylinder 62. When the balloon for attachment 66 is expanded as shown in FIG. 6, the inner diameter of a swelled part (which is a part having the smallest inner diameter) of the balloon for attachment 66 is smaller than the outer diameter D2 of the insert part 12, so that the balloon for attachment 66 presses the whole outer circumferential surface of the insert part 12. In this way, the cylinder body 62 can be fixed to the insert part 12 and a ring-shaped gap between the inner circumferential surface of the cylinder body 62 and the outer circumferential surface of the insert part 12 can be sealed by the balloon for attachment 66.

It is preferable that the balloon for attachment 66 is easier to expand than the balloon 60. For example, thickness of the balloon for attachment 66 may be formed thinner than thickness of the balloon 60 or elongation percentage of the balloon for attachment 66 may be set larger than elongation percentage of the balloon 60.

The branch passage 63C is provided with an elastic piece 68 as a check valve. The elastic piece 68 is provided so that its one end is fixed to the cylinder body 62 and shuts the branch passage 63C, as shown in FIGS. 4 and 5. When fluid is supplied through the branch passage 63C to the balloon for attachment 66, the elastic piece 68 is elastically deformed to allow fluid to flow through, as shown in FIG. 6. When pressure of fluid in the branch passage 68C decreases, the elastic piece 68 returns to its original shape and shuts the branch passage 68C to prevent backflow of fluid. Therefore, contraction of the expanded balloon for attachment 66 can be prevented. The configuration for the check valve is not limited to the above described configuration and any configuration may be employed which allows fluid supply to the balloon for attachment 66 and prevents fluid discharge from the balloon for attachment 66.

As shown in FIG. 5, a connector is formed in the end 63B of the flow passage 63 and an end 64B of a tube 64 is detachably coupled to the connector. A lure-lock mechanism is used for the connector, for example. Thus, the end 63B and the end 64B can be coupled while maintaining air-tightness between the tube 64 and the flow passage 63.

As shown in FIG. 1, a connector is provided at an end 64A on a base end side of the tube 64 and a tube 110 of the balloon controlling apparatus 100 is detachably coupled to the connector. Therefore, air can be supplied and sucked through the tubes 110, 64 to/from the flow passage 63 of the cylinder body 62 by supplying and sucking fluid (air, for example) from/to the balloon controlling apparatus 100. Thereby, the balloon for attachment 66 can be expanded to fix the cylinder body 62 to the insert part 12 so that the balloon 60 is fixed to the insert part 12, and air can be supplied to/sucked from the balloon 60. The balloon 60 expands in a generally spherical shape by supplying air and sticks on the outer surface of the insert part 12 by sucking air. The method of expanding the balloon for attachment 66 in order to fix the balloon 60 to the insert part 12 will be described later.

After the balloon 60 is fixed to the insert part 12, the tube 64 may be placed along the insert part 12 and fixed to the insert part 12 with a tape and the like. Further, the end 64A on the base end side of the tube 64 may be engaged to an engaging part which may be provided in the hand operating part 14.

The balloon controlling apparatus 100 is an apparatus for supplying and sucking fluid such as air to/from the balloon 60. The balloon controlling apparatus 100 mainly includes an apparatus body 102 and a hand switch 104 for remote control.

On a front side of the apparatus body 102, a power switch SW1, a stop switch SW2, and a pressure displaying part 106 are provided. The pressure displaying part 106 is a panel on which pressure value of the balloon 60 is indicated. If an abnormal condition such as rupture of the balloon occurs, an error code is indicated on the pressure displaying part 106.

The tube 110 for supplying and sucking air to/from the balloon 60 is connected to the front side of the apparatus body 102. At the connection part of the tube 110 and the apparatus body 102, an anti-backflow unit 112 is provided for preventing backflow of body fluid in case of rupture of the balloon 60. The anti-backflow unit 112 is configured by incorporating a filter for gas-liquid separation in a hollow disk-like case (not shown) which is detachably attached to the apparatus body 102. Fluid flow into the apparatus body 102 is prevented by the filter.

On the hand switch 104, various switches are provided. For example, a stop switch which is similar to the stop switch SW2 on the apparatus body 102, an on/off switch for directing pressurization/depressurization of the balloon 60, and a pause switch for keeping pressure of the balloon 60 are provided. The hand switch 104 is electrically connected via a cord 130 to the apparatus body 102. Although not shown in FIG. 1, the hand switch 104 is provided with an indicating part on which air supply or discharge conditions of the balloon 60 are indicated.

The balloon controlling apparatus 100 configured in the above described manner supplies air to the balloon 60 in order to expand it and keeps the expanded condition of the balloon 60 by controlling to keep air pressure at a constant value. In addition, the balloon controlling apparatus 100 sucks air from the balloon 60 in order to contract it and keeps the contracted condition of the balloon 60 by controlling to keep air pressure at a constant value.

The balloon controlling apparatus 100 is connected to a balloon-specific monitor 82, on which the pressure value and the expanded and contracted conditions of the balloon 60 are displayed when the balloon 60 is expanded and contracted. The pressure value and the expanded and contracted conditions of the balloon 60 may be displayed on a monitor 50 in such a manner that they are superimposed on observed images of the endoscope 10.

Then, the method of attaching the balloon 60 configured in the above described manner will be described.

At first, the insert part 12 is inserted through the cylinder body 62 of the balloon 60, as shown in FIGS. 2, 3. Because the inner diameter D3 of the balloon for attachment 66 is formed larger than the outer diameter D2 of the insert part 12, the insert part 12 can be easily inserted through the cylinder body 62.

Figure 7:
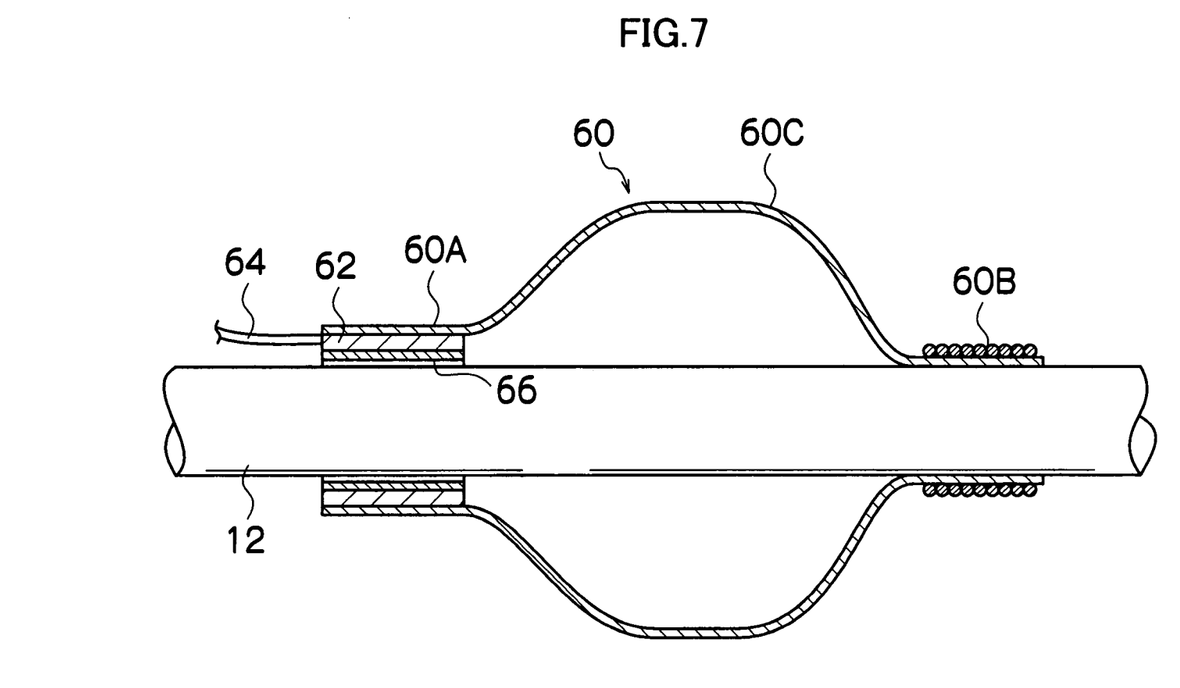
FIG. 7 is a cross sectional view showing the balloon unit through which the insert part is inserted.

Next, the insert part 12 is inserted through the end 60B of the balloon 60, as shown in FIG. 7. When the cylinder body 62 is grasped and relatively moved toward the base end of the insert part 12, the insert part 12 enlarges the end 60B and thus the insert part 12 can be automatically inserted through the end 60B.

After the balloon 60 is placed in a predetermined attachment position on the insert part 12, thread is wound around the end 60B of the balloon 60 so that the end 60B of the balloon 60 is fixed to the insert part 12. The end 60B may be fixed to the insert part 12 by fitting a fixing ring and the like over the end 60B.

Then, the end 64B of the tube 64 is coupled to the end 63B of the flow passage 63 of the cylinder body 62, as shown in FIG. 5. Then, air is supplied to the flow passage 63 of the cylinder body 62 by the balloon controlling apparatus 100. Thereby, air is supplied into the balloon for attachment 66 which is communicated with the flow passage 63. Accordingly, the balloon for attachment 66 expands and presses the whole outer circumferential surface of the insert part 12 so that the cylinder body 62 is fixed to the insert part 12 via the balloon for attachment 66, as shown in FIG. 6. A gap between the inner circumferential surface of the cylinder body 62 and the outer circumferential surface of the insert part 12 is sealed by the balloon for attachment 66. Thus, the balloon 60 is fixed to the insert part 12 in such a manner that the ends 60A, 60B of the balloon 60 hermetically contact the insert part 12.

After the balloon 60 is fixed to the insert part 12, air is sucked from the balloon 60 by the balloon controlling apparatus 100 to contract the balloon 60. In doing so, the balloon for attachment 66 does not contract because the cylinder body 62 is provided with the elastic piece 68, and therefore the balloon for attachment 66 can be always kept expanded and fixed to the insert part 12.

As described above, in the balloon 60 of this embodiment, the end 60A is fitted over and fixed to the cylinder body 62. Therefore, the insert part 12 can be easily covered with the end 60A of the balloon 60 by inserting the insert part 12 through the cylinder body 62 and thus the task of attaching the balloon 60 can be easily performed.

In addition, according to this embodiment, because the flow passage 63 is formed in the cylinder body 62, fluid can be supplied to the balloon 60 by connecting the tube 64 to the flow passage 63. Therefore, it is not necessary to insert a tip of the tube 64 deeply into the balloon 60 and thus the task of attaching the balloon 60 can be easily performed and air-tightness in the end 60A of the balloon 60 can be improved.

Further, according to this embodiment, because the cylinder body 62 is fixed to the insert part 12 by providing the balloon for attachment 66 on the inner side of the cylinder body 62 and expanding the balloon for attachment 66, the fixing to the insert part 12 can be reliably performed even if the outer diameter dimension of the insert part 12 varies. Further, the feature of expanding and fixing the balloon for attachment 66 allows large clearance between the inner circumferential surface of the cylinder body 62 and the outer circumferential surface of the insert part 12, so that the insert part 12 can be easily inserted through the cylinder body 62. Moreover, when the balloon for attachment 66 is expanded and fixed to the insert part 12, air-tightness between the insert part 12 and the cylinder body 62 can be kept by the balloon for attachment 66.

Moreover, according to this embodiment, because the flow passage 63 of the cylinder body 62 is branched to communicate with both the balloon 60 and the balloon for attachment 66, the balloon 60 and the balloon for attachment 66 are expanded with a common fluid. Therefore, the number of tubes 64 extending from the cylinder body 62 can be reduced.

In one exemplary method of operating the endoscope apparatus configured in the above described manner, the insert part 12 is inserted by pushing and the balloon 60 is expanded to fix the insert part 12 to a viscera (large bowel, for example), as required. Then, after the insert part 12 is drawn to simplify a tubular shape of the viscera, the balloon 60 is contracted to further insert the insert part 12 deeply into the viscera (large bowel, for example). For example, the insert part 12 is inserted from the anus of a subject and the balloon 60 is expanded to fix the insert part 12 to the bowel when the tip of the insert part 12 passes through the colon sigmoideum. Then, the insert part 12 is drawn to make the colon sigmoideum into a generally linear shape. Thereafter, the balloon 60 is contracted and the tip of the insert part 12 is inserted deeply into the bowel. In this way, the insert part 12 can be easily inserted deeply into the bowel.

Although a common fluid is supplied to both the balloon 60 and the balloon for attachment 66 by providing the branch passage 63C of the flow passage 63 in the cylinder body 62 in the above described embodiment, this is not limiting. For example, by separately providing a tube which is communicated with the balloon for attachment 66, fluid may be supplied to the balloon for attachment 66 independent of the balloon 60 so that the balloon for attachment 66 is independently expanded. In this case, it is preferable that fluid having larger viscosity is supplied to the balloon for attachment 66 than that of the balloon 60 or the balloon for attachment 66 is expanded with higher pressure than that of the balloon 60. Alternatively, it is preferable that liquid (water, for example) is supplied to the balloon for attachment 66 while gas (air, for example) is supplied to the balloon 60. In this way, the fixing to the insert part 12 by the balloon for attachment 66 can be done firmly and it is reliably prevented that fluid leaks from the balloon 60 when the balloon 60 is expanded.

Figure 8:
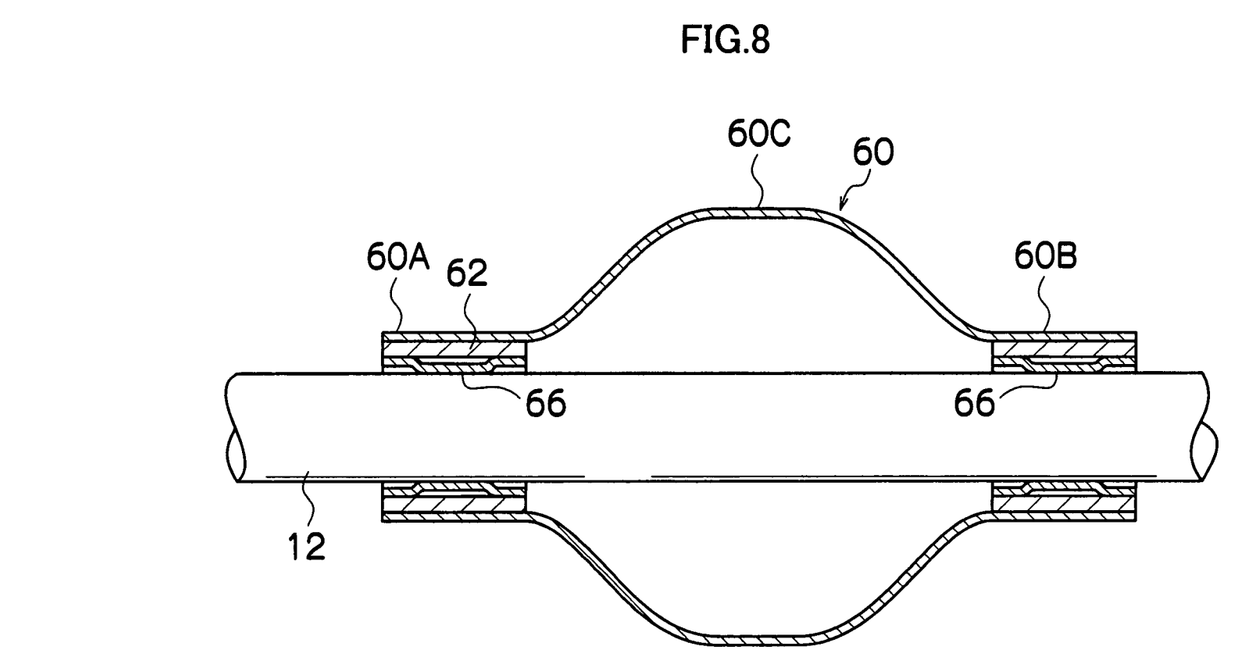
FIG. 8 is a cross sectional view showing a balloon unit in which cylinder bodies are covered with both ends for fixing.

Although the cylinder body 62 is covered with the end 60A of the balloon 60 in the above described embodiment, the cylinder bodies 62, 62 may be covered with both ends 60A, 60B of the balloon 60, as shown in FIG. 8. By covering the cylinder bodies 62 with both ends 60A, 60B in this way, the insert part 12 can be more easily inserted through the balloon 60 and the task of attaching the balloon 60 can be quickly performed. In the case of the balloon unit in FIG. 8, it is preferable that the balloons for attachment 66, 66 provided on both cylinder bodies 62, 62 are configured to couple to each other so that both balloons for attachment 66, 66 are simultaneously expanded and contracted. Further, in the case of the balloon unit in FIG. 8, it is preferable that the both cylinder bodies 62, 62 are configured to detachably engage to each other at their opposite end surfaces and the insert part 12 is inserted through in their engaged condition and the engagement is released after inserting.

Although the cylinder body 62 is fixed to the insert part 12 by the balloon for attachment 66 in the above described embodiment, the approach of fixing the cylinder body 62 to the insert part 12 is not limited to this, and a tape and the like may be wound for fixing.

Although the balloon 60 is formed in a generally cylindrical shape in the above described embodiment, the shape of the balloon 60 is not limited to this and any shape having a cylindrical end may be employed. Therefore, the balloon may be formed in a bag shape, for example.

Figure 9:
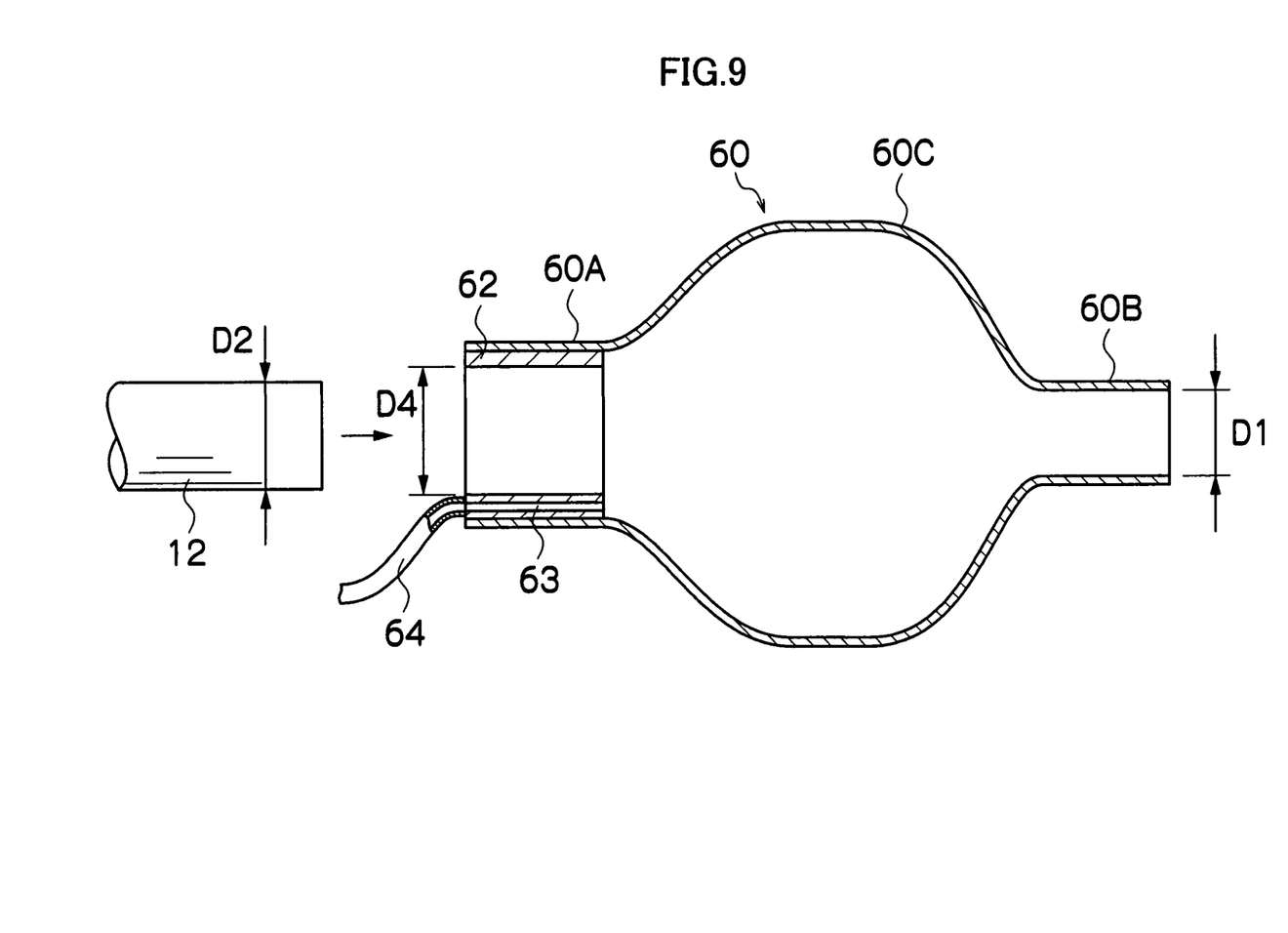
FIG. 9 is a cross sectional view showing a balloon unit in another embodiment.

Although the balloon 60 and the cylinder body 62 are configured as a balloon unit in the above described embodiment, this is not limiting. The balloon 60, the cylinder body 62, and the tube 64 may be configured as a balloon unit by integrally fixing the tube 64 to the cylinder body 62, as shown in FIG. 9. In this case, an end of the tube 64 may be embedded and fixed in the cylinder body 62 and the flow passage 63 may be formed by the tube 64.

In the balloon unit shown in FIG. 9, in contrast to the balloon unit shown in FIGS. 2 to 6, there is no balloon for attachment 66 and further the flow passage 63 of the cylinder body 62 is not branched and it is formed to penetrate in an axial direction of the cylinder body 62. In such a balloon unit, the inner diameter D4 of the cylinder body 62 may be configured to be somewhat larger than the outer diameter D2 of the insert part 12. In this way, the insert part 12 can be easily inserted through the cylinder body 62.

Figure 10:
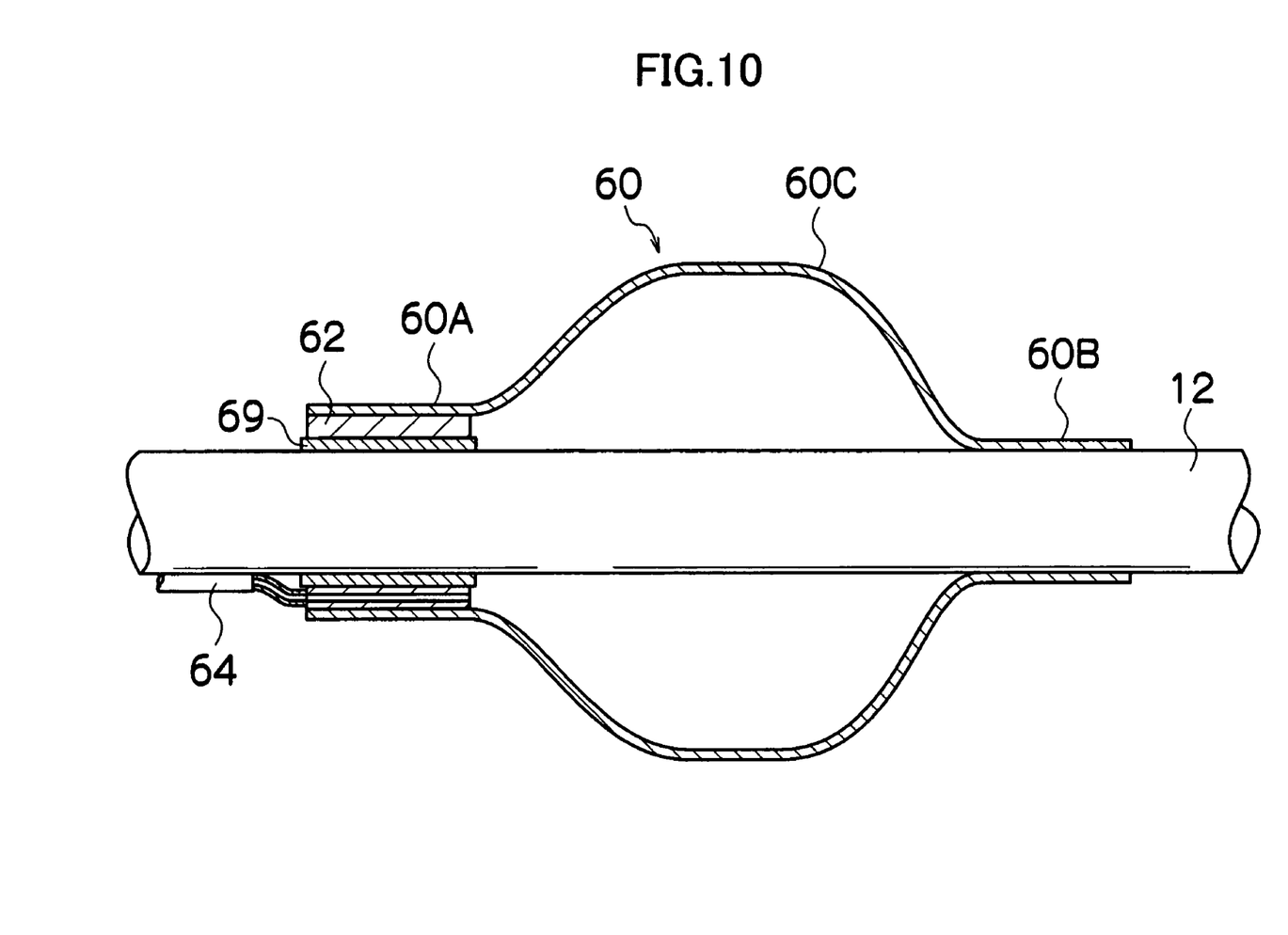
FIG. 10 is a cross sectional view showing an attachment condition of the balloon unit in FIG. 9.

When the balloon unit in FIG. 9 is attached to the insert part 12, it is preferable that a seal tape 69 is wound around the outer circumferential surface of the insert part 12 (the soft part 40, for example) as shown in FIG. 10, so that the cylinder body 62 is fitted and fixed in the wound portion. In this way, a gap between the inner circumferential surface of the cylinder body 62 and the outer circumferential surface of the insert part 12 can be sealed by the seal tape 69. In the balloon unit in FIG. 10, in order to prevent misalignment of the balloon 60, it is preferable that a fluorine tape (not shown) or the like is wound over the ends 60A, 60B of the balloon 60 and the tube 64 to reliably fix to the insert part 12.

Although the example of attaching the balloon unit for an endoscope apparatus according to the present invention to the insert part 12 of the endoscope 10 has been described in the above described embodiment, the object to which the balloon is attached is not limited to the endoscope, but may be any instrument used in the endoscope apparatus, such as an insert supporter for endoscope or an endoscope operative instrument.

What is claimed is:
1. A balloon unit for an endoscope apparatus comprising:
a first balloon for an endoscope apparatus having first and second openings and opposing each other at opposite ends of a bulbous region, each of said first and second openings having a different diameter than an inner diameter of said bulbous region so as to be formed in a cylindrical shape in which an insert member including one of an insert part of an endoscope and an insert supporter having the insert part inserted therein is inserted; and
a cylinder body separate from said insert member and having an inner diameter larger than an outer diameter of the insert member; wherein
the first opening of the first balloon is fitted over and fixed to the insert member therein; and
the second opening of the first balloon is fitted over and affixed to the cylinder body to form a unit and the unit is attached to the insert member or detached from the insert member; and wherein
a flow passage for supplying and sucking fluid into/from the balloon for an endoscope apparatus is formed in the cylinder body;
a second balloon for attachment, through which the insert member is inserted, is provided on an inner side of the cylinder body, the cylinder body is fixed to the insert member by expanding the second balloon for attachment so that the second balloon for attachment presses an outer circumferential surface of the insert member, and further the flow passage of the cylinder body is branched to communicate with the second balloon for attachment; and a branch passage of the flow passage is provided with a check valve that prevents the fluid from flowing out from the second balloon for attachment.

2. The balloon unit for an endoscope apparatus according to claim 1, wherein
a tube for supplying and sucking fluid into/from the first balloon for an endoscope apparatus is connected to the cylinder body.

3. The balloon unit for an endoscope apparatus according to claim 1, wherein
in the end of the flow passage of the cylinder body, a connector is provided to which the tube is detachably connected.

4. The balloon unit for an endoscope apparatus according to claim 1, wherein
said second balloon for attachment is a doughnut-shaped balloon.

\* \* \* \* \*